United States Patent [19]
Leduc et al.

[11] Patent Number: 5,549,911
[45] Date of Patent: Aug. 27, 1996

[54] GALENIC FORM OF 5-NITROMIDAZOLE DERIVATIVES WHICH IS EFFECTIVE FOR THE TREATMENT OF PARASITOSES AND INFECTIONS OF THE ENTIRE GASTROINTESTINAL TRACT

[75] Inventors: Gérard Leduc, Malesherbes; Patrice Debregeas, Paris, both of France

[73] Assignee: Laboratoires Des Produits Ethiques Ethypharm, Houdan, France

[21] Appl. No.: 371,520

[22] Filed: Jan. 11, 1995

[51] Int. Cl.$^6$ .............................. A61K 9/22; A61K 9/26; A61K 9/52; A61K 9/54
[52] U.S. Cl. .................. 424/458; 424/468; 424/469; 424/470; 424/489; 424/490
[58] Field of Search ........................... 424/458, 468, 424/469, 470, 489, 490

[56] References Cited

FOREIGN PATENT DOCUMENTS

| | | |
|---|---|---|
| 206625A2 | 6/1986 | European Pat. Off. . |
| 348808A2 | 6/1989 | European Pat. Off. . |
| 348808A3 | 6/1989 | European Pat. Off. . |
| 348808B1 | 6/1989 | European Pat. Off. . |
| 8903219 | 4/1989 | WIPO . |
| 9102518 | 3/1991 | WIPO . |
| 9201457 | 2/1992 | WIPO . |
| 9211848 | 7/1992 | WIPO . |
| 9318755 | 9/1993 | WIPO . |
| 9408594 | 4/1994 | WIPO . |

OTHER PUBLICATIONS

Lambov et al Pharmazie 49(6): 438–440 (1994) (pp. 26–27).
Shell WO/PCT93/18755111 (Sep. 30, 1993).
Tsankov et al Pharm, Ind. 53(7): 695–698 (1991) (p. 31).
Chemtob et al I Drug Dev. Ind. Pharm. 15(8): 1161–1174 (1989).
Leucata et al I Clujul Med. 59(4): 348–352 (1986).
Leucata et al II Clujul Med. 59(1): 74–79 (1986).
Mandal et al. Indian Drugs 23(7): 400–403 (1986).
Chemtob et al (II) Int. J. Pharm. 29(1): 1–7 (1986).
Chemtob et al (III) Int. J. Pharm. 29(1): 83–92 (1986).
WO91/17744–PCT International Application Publication––Gary R. Jernberg, 1981.
Chemical Abstracts, vol. 94, No. 12, abstract No. 90226w; "icroencapsulation of metronidazol" (1981).
Indian J. Pharm Sci., vol. 42, No. 2, M. R. Baichwal Et Al.; "Microencapsulation Of Metronidazole" (1980).

*Primary Examiner*—Shep K. Rose
*Attorney, Agent, or Firm*—Dressler, Goldsmith, Milnamow & Katz, Ltd.

[57] ABSTRACT

The present invention relates to a galenic form of 5-nitroimidazole derivatives which is characterized in that it comprises a combination of microgranules of 5-nitroimidazole derivatives consisting, on the one hand, of gastroresistant microgranules and, on the other hand, of prolonged-release microgranules, the pharmaceutical compositions comprising them and the microgranules as intermediates in the preparation of the form according to the invention.

22 Claims, No Drawings

GALENIC FORM OF 5-NITROMIDAZOLE DERIVATIVES WHICH IS EFFECTIVE FOR THE TREATMENT OF PARASITOSES AND INFECTIONS OF THE ENTIRE GASTROINTESTINAL TRACT

The present invention relates to a new galenic form of 5-nitrolmldazole derivatives which is effective for the treatment of parasitoses and infections of the entire gastrointestinal tract.

It relates more particularly to a new galenic form intended for the treatment of parasitoses and infections exhibiting resistant forms in the lower part of the intestinal tract, especially in the sigmoid colon and rectum.

Parasitoses of the intestines such as amoebiasis, colic parasitosis which may become complicated with extra intestinal locations, exhibit in the lower part of the intestines resistant forms which are responsible for the transmission of these conditions.

In the case of amoebiasis, they are Entamoebacter histolytica cysts. These cysts which are present in the lower part of the digestive tube of the infected subjects are excreted with the faecal materials. The lack of personal and collective hygiene ensures propagation of the disease as well as self-reinfection of individuals who are carriers of these parasites.

Entamoebacter histolytica also exists in a more labile form, Entamoebacter histolytica minuta, which does not cause any lesion but can be converted into a pathogenic form, Entamoebacter histolytica histolytica, which penetrates the intestinal mucous membrane and causes the propagation of the disease, both in the upper part of the intestines and in the lower part, in the form of cysts. This form is also responsible for the most widespread complications of amoebiasis, which migrate into the liver or even into the lungs or the brain.

It is possible to treat rapidly parasitoses and infections of the intestinal tract with medicinal products as used for the treatment of tourista. However, these treatments not being applicable systematically, they do not take into account the problems of hygiene which are responsible for the propagation of these diseases.

Likewise, routine and inexpensive treatments of amoebiasis with azole-containing derivatives, in particular 5-nitroimidazole derivatives (metronidazole, secnidazole and the like), exist. However, these treatments, which are effective against conditions of the upper part of the intestines, against the miuuta and histolytica forms, are not very effective for the treatment of cysts. Moreover, these 5-nitroimidazole derivatives, administered in too large quantities, are absorbed in the upper part of the digestive tube, which can cause unpleasant side effects (metallic taste in the mouth), or even toxic effects.

Other conditions which develop resistant forms in the lower part of the intestines can also be treated, with the same drawbacks, with 5-nitroimidazole derivatives. They are for example infections caused by Helicobacter pilori, a bacterium present in the stomach and in the downstream part of the digestive tube and which is implicated in the pathogenesis of gastritis and of gastric and duodenal ulcer, the irritation caused by Helicobacter causing an acidic hypersecretion of the stomach which results in ulceration of the gastric and duodenal membranes. Its participation has also been mentioned in the genesis of digestive cancers.

Given the increasing importance of parasitoses and infections of the entire gastrointestinal tract, it was becoming important to find an inexpensive treatment taking into account the problems of transmission of the conditions linked to lack of hygiene, that is to say which make it possible to treat effectively the resistant forms present in the lower part of the intestines.

In order to solve these various problems, the present invention therefore relates to a new galenic form of 5-nitroimidazole derivatives.

The form according to the invention comprises a combination of microgranules of 5-nitroimidazole derivatives consisting, on the one hand, of gastroresistant microgranules and, on the other hand, of prolonged-release microgranules.

The gastroresistant microgranules are intended to ensure the efficacy of the form according to the invention essentially in the upper part of the gastrointestinal tract, whereas the prolonged-release microgranules act essentially in its lower part.

The ratio of the various microgranules will be appropriate to the desired effect, favouring action of the form according to the invention essentially in the lower or upper part of the tract, or alternatively so as to ensure a constant action over its entire length. It will also depend on the excipients used for preparing the microgranules.

The gastroresistant microgranule/prolonged-release microgranule weight ratio is between $6/4$ and $1/9$, advantageously between $4/6$ and $1/9$. Preferably, in order to ensure a high efficacy of the form according to the invention on conditions of the lower part of the intestines, the gastroresistant microgranule/prolonged-release microgranule ratio is between $25/75$ and $15/85$.

In order to ensure a high efficacy of the form according to the invention, the combined microgranules should correspond to the following dissolution patterns:

| gastroresistant microgranules: | |
| --- | --- |
| 2 hours in 0.1 N HCl | <15% |
| 1 hour at pH 6.0 | >75% |
| prolonged-release microgranules: | |
| 2 hours in 0.1 N HCl | <15% |
| 1 hour at $6.8 \leq pH \leq 7.5$ | <50% |
| 4 hours at $6.8 \leq pH \leq 7.5$ | 40% to 90% |
| 6 hours at $6.8 \leq pH \leq 7.5$ | >70% | the percentages being given by weight of active ingredient dissolved relative to the total weight before dissolution.

The microgranules which are useful in the form according to the invention all advantageously consist of a neutral granular carrier coated with an active layer consisting of a mixture of active ingredient, 5-nitro-imidazole derivative and a binding agent.

The neutral carrier advantageously consists of particles of starch and of a mixture of starch and sucrose which have an average diameter of between 400 and 800 microns.

The 5-nitroimidazole derivative is advantageously chosen from metronidazole, secnidazole, tinidazole and mixtures thereof.

The binding agent is a customary agent known for its use in the preparation of microgranules, advantageously chosen from polyvinylpyrrolidone of various molecular weights (preferably K30 and K17 Kollidon grades (manufactured by BASF); the grade corresponds to the value of the constant K which is a function of the molecular weight and the viscosity of the product. The constant K is the subject of specifications in the various official monographs in current usage, as regards polyvinylpyrrolidone); from hydroxypropyl methylcellulose of various molecular weights (preferably grade 615; the HPMC grades are a function of the level of substitution of the product with Methoxy and Hydroxypropoxy groups and reflect the viscosity. The various grades are described in the official monographs of this product, in particular in USP XXII); from hydroxypropyl cellulose of various molecular weights, from poly(meth)acrylic esters (marketed by RÖHM GmbH under the trade mark EUDRAGIT®), and mixtures thereof.

Of course, the present invention also applies to microgranules comprising a core simply consisting of the active ingredient and a binding agent.

The gastroresistant and prolonged-release micro-granules differ in their external layer of coating of the active layer. This will be, on the one hand, a gastro-resistant external layer for the gastroresistant microgranules and, on the other hand, a prolonged-release external layer for the prolonged-release microgranules.

The gastroresistant external layer consists of the customary excipients used in the technique for the preparation of gastroresistant microgranules. It comprises excipients ensuring the resistance of the coating to pH values of less than 5.0, which are advantageously chosen from poly(meth)acrylic esters (marketed by RöHM under the trade marks EUDRAGIT® L 100-55, EUDRAGIT® L 100, EUDRAGIT® L 30D-55), hydroxypropyl methylcellulose phthalate (marketed by the company SHIN ETSU Chemical Co., Ltd. under the trade marks HP 50® and HP 55®), and mixtures thereof.

The prolonged-release external layer comprises, for its part, the customary excipients used in the technique for the preparation of prolonged-release microgranules, independent of the pH of the medium in which they act, advantageously chosen from poly(meth)acrylic esters (marketed by RÖHM under the trade marks EUDRAGIT® RS 100, EUDRAGIT® RS 30D), ethyl cellulose (marketed by FMC Corporation, Philadelphia under the trade mark AQUACOAT®), and mixtures thereof. In this case, it is the transit time of the microgranules in the intestines which will determine the time of release of the active ingredient.

The prolonged-release external layer may also comprise an excipient which is dependent on the pH of the medium in which the microgranules transit, in particular the pH-dependent poly(meth)acrylic esters (marketed by RÖHM under the trade mark EUDRAGIT® S). In this case, it is no longer the transit time of the microgranules which will determine the time of release of the active ingredient, but the pH of the medium in which they transit. Thus, in order to ensure the release of the active ingredient in the lower part of the intestines, an excipient which is soluble at pH values greater than 7, such as EUDRAGIT® S, will be chosen. Of course, depending on the desired effect, the prolonged-release microgranules may also consist of a mixture of pH-dependent release microgranules, so as to release the active ingredient at various pH values, or alternatively of a mixture of microgranules dependent or not dependent on the pH, modulating a release as a function of the transit time and the pH.

The gastroresistant external layer and the prolonged-release external layer may also comprise customary additives, such as talc which facilitates the coating by its lubricating properties or derivatives of silica or stearic acid, and/or one or more plasticizers which facilitate good formation of the coating film, especially (poly)carboxylic acid esters such as citric acid esters (especially triethyl citrate), dibutyl sebacate and mixtures thereof.

Given the importance of the size of the microgranules with respect to their rate of transit in the intestines, the average diameter of the microgranules which are useful for the form according to the invention is advantageously between 0.4 and 1.5 mm, preferably of between 0.8 and 1.1 mm.

The microgranules which are useful in the form according to the invention are advantageously prepared according to the following general scheme:

coating of the neutral core with the active layer, coating of the active layer either with a gastroresistant layer or with a prolonged-release layer according to the microgranules, screening, and drying.

The microgranules are then mixed according to the desired proportions and packaged in a form appropriate for its administration, in particular in the form of tablets, of rapidly-disintegrating tablets, of gelatin capsules or alternatively in sachets.

The present invention therefore relates to a pharmaceutical composition comprising the form described above.

It also relates, as intermediate products in the preparation of the galenic form according to the invention, to the gastro-protected and prolonged-release microgranules described above.

Of course, since the gastro-resistant and prolonged-release microgranules are prepared and can be packaged separately, the present invention also relates to a combination product comprising microgranules of gastro-protected 5-nitroimidazole derivatives and microgranules of prolonged-release 5-nitroimidazole derivatives as described above for use as a combination simultaneously, separately or spaced out over time for the treatment of parasitoses and infections of the gastrointestinal tract, in particular amoebiases and infections linked to the presence of Helicobacter pilori.

Other characteristics of the new form according to the invention will emerge in the light of the examples below.

EXAMPLE 1: ⅔ mixture of metronidazole microgranules

The following mixture was prepared:

|  | A % | B % |
| --- | --- | --- |
| Metronidazole | 63.8 | 64.5 |
| Neutral core | 21.3 | 21.5 |
| PVP K30 | 5.7 | 5.7 |
| HP50 | 9.2 | 4.7 |
| Ethyl cellulose N7 | — | 1.8 |
| Talc | — | 1.8 |
|  | 100.0 | 100.0 |

The percentages are given by weight relative to the total weight of the microgranules. Ingredients:

Neutral core: composed of sucrose (about 75%) and maize starch (about 25%)

PVP: Polyvinylpyrrolidone K30

HP 50: Hydroxypropyl methylcellulose phthalate, dissolution from pH 5.0

Ethyl cellulose N7: Ethyl cellulose whose grade N7 represents the viscosity of the product.

The microgranules were prepared according to the procedure described later.

EXAMPLE 2: 3/7 mixture of metronidazole microgranules

The following mixture was prepared according to the same procedure:

|  | A % | B % |
|---|---|---|
| Metronidazole | 52.6 | 56.9 |
| Neutral core | 19.9 | 21.6 |
| PVP K30 | 2.7 | 2.8 |
| EUDRAGIT ® L30D-55 | 11.8 | — |
| Triethyl citrate | 1.2 | 3.7 |
| Talc | 11.8 | 7.5 |
| EUDRAGIT ® S | — | 7.5 |
|  | 100.0 | 100.0 |

The percentages are given by weight relative to the total weight of the microgranules. Ingredients:

Neutral core: composed of sucrose (about 75%) and maize starch (about 25%)

PVP: Polyvinylpyrrolidone K30

EUDRAGIT® L30D-55: Aqueous dispersion of type C methacrylic acid copolymers; dissolution from pH 5.5

Talc

EUDRAGIT® S: Type B methacrylic acid copolymer; dissolution from pH 7.0.

EXAMPLE 3: 25/75 mixture of metronidazole microgranules

The following mixture was prepared according to the same procedure:

|  | A % | B % |
|---|---|---|
| Metronidazole | 51.8 | 59.7 |
| Neutral core | 19.6 | 22.6 |
| EUDRAGIT ® E 100 | 3.4 | 3.9 |
| EUDRAGIT ® L30D-55 | 12.0 | — |
| EUDRAGIT ® RS 30D | — | 6.3 |
| Triethyl citrate | 1.2 | 1.2 |
| Talc | 12.0 | 6.3 |
|  | 100.0 | 100.0 |

The percentages are given by weight relative to the total weight of the microgranules. Ingredients:

Neutral core: Composed of sucrose (about 75%) and maize starch (about 25%)

EUDRAGIT® E 100: Methacrylic acid copolymer used here as binder

EUDRAGIT® L30D-55

EUDRAGIT® RS 30D: Aqueous dispersion of type B methacrylic acid copolymers; prolonged-release dissolution.

Talc.

EXAMPLE 4: Mixture corresponding to batch XM285

The following mixture was prepared according to the same procedure:

Composition of the batch XM 285:

| Metronidazole: | 65.1% |
|---|---|
| Neutral core: | 21.7% |
| PVP K30: | 4.8% |
| Ethyl cellulose N7: | 1.3% |
| HP 50: | 5.0% |
| Ethyl cellulose N7: | 1.3% |
| Triethyl citrate: | 0.5% |
| Talc: | 1.6% |
|  | 100.0% |

EXAMPLE 5: Secnidazole formulation

The following mixture was prepared according to the same procedure.

|  | A | B |
|---|---|---|
| Secnidazole | 47.8% | 45.5% |
| Neutral core | 33.0% | 31.9% |
| PVP K17 | 3.4% | 3.2% |
| EUDRAGIT ® L30D-55 | 12.6% | — |
| EUDRAGIT ® RS30D | — | 10.5% |
| Triethyl citrate | 1.3% | 2.1% |
| Talc | 1.9% | 6.8% |
|  | 100.0 | 100.0 |

Mixture of 25% of A and 75% of B

Dissolution patterns

Dissolution tests of the forms of Examples 1 and 4 were carried out in a 0.1N HCl solution and at pH 6.8. The results are given in the table below. The percentages are given by weight of microgranules dissolved relative to the total weight of microgranules before dissolution.

|  | Example 1 | Example 4 |
|---|---|---|
| Gastroresistance test |  |  |
| 0.1N HCl for 2 hours | 6.7% | 8.5% |
| Dissolution test pH 6.8 |  |  |
| 1 Hour | 42.2% | 47.2% |
| 4 Hours | 78.2% | 72.3% |
| 6 Hours | 86.9% | 81.5% |

Clinical trials

A clinical study of the efficacy of the form according to the invention was carried out on 60 patients of both sexes, aged 15 to 75 years and suffering from amoebiasis exhibiting cystic forms in the colon.

The study was carried out according to a rigorous "randomized", double placebo and double blind methodology by comparing the form of Example 1 to the metronidazole marketed under the trade mark Flagyl.

The administered doses were 1.5 g/day (3 daily doses of two gelatin capsules containing 250 mg doses of metronidazole) for 10 days.

The results of this study show a cure rate of 85% for the form according to the invention against 14% for Flagyl.

Procedure for the manufacture of metronidazole microgranules (batch XM 415/2)

Phase 1: Preparation of the binding solution: alcoholic solution of PVP at 20% in alcohol the solution is prepared in a stainless steel mixer, pour the 95% ethyl alcohol into the mixer, initiate stirring and incorporate the PVP in small quantities, maintain the stirring until complete dissolution is obtained.

Phase 2: Application place the neutral carrier grains in the rotating turbine, the application is performed by dusting the active ingredient over the neutral microgranules, alternating with sequences of spraying of the binding solution, screening the mass of microgranules, (screens which can be used: mesh opening 0.50; 0.71; 0.99; 1.12; 1.25 mm), dry the microgranules by blowing hot air inside the rotating turbine.

Phase 3: Separation of the mass into two parts divide the mass into two parts A and B corresponding respectively to 75% and 25% of the mass of microgranules, place each of the two parts in a different turbine.

Phase 4: Preparation of the premounting solution:

alcoholic solution of ethylcellulose N7 at 10% the solution is prepared in a stainless steel mixer, pour the 95% ethyl alcohol into the mixer, initiate stirring and incorporate the ethylcellulose in small quantities maintain the stirring until complete dissolution is obtained.

Phase 5: Premounting of part A apply the premounting solution over the micro granules by spraying, sprinkle the talc simultaneously, screen the mass of microgranules, (screens which can be used: mesh opening 0.50; 0.71; 0.99; 1.12; 1.25 mm)

dry the microgranules by blowing hot air inside the rotating turbine.

Phase 6: Preparation of the coating solution: aceto-alcoholic solution (20/80) of HP 50 at 7.5% the solution is prepared in a stainless steel mixer, pour the 95% ethyl alcohol and then the acetone into the mixer, initiate stirring and incorporate the HP 50 in small quantities, maintain the stirring until complete dissolution is obtained.

Phase 7: Coating of parts A and B: the coating is carried out with a time interval over parts A and B apply the coating solution over the microgranules by spraying, screen the mass of microgranules, (screens which can be used: mesh opening 0.50; 0.71; 0.99; 1.12; 1.25 mm)

dry the microgranules by blowing hot air inside the rotating turbine

Phase 8: Lubrication—mixing of the two parts introduce the two parts A and B as well as the lubricating talc into the rotating turbine, mix the mass, stop the turbine.

The new galenic form according to the invention appears also usefull in the preventive treatment of infections with anaerobic germs during surgical operation with high risks of such type of infections like digestive surgery, etc.

We claim:

1. Galenic form of 5-nitroimidazole derivatives characterized in that it comprises a combination of microgranules of 5-nitroimidazole derivatives consisting of gastroresistant microgranules and prolonged-release microgranules.

2. Galenic form according to claim 1, characterized in that the gastroresistant microgranule/prolonged-release microgranule weight ratio is between 6/4 and 1/9.

3. Galenic form according to claim 2, characterized in that the gastroresistant microgranule/prolonged-release microgranule weight ratio is between 25/75 and 15/85.

4. Galenic form according to claim 1 characterized in that the combined microgranules correspond to the following dissolution patterns:

| gastroresistant microgranules: | |
|---|---|
| 2 hours in 0.1 N HCl | <15% |
| 1 hour at pH 6.0 | >75% |
| prolonged-release microgranules: | |
| 2 hours in 0.1 N HCl | <15% |
| 1 hour at $6.8 \leq pH \leq 7.5$ | <50% |
| 4 hours at $6.8 \leq pH \leq 7.5$ | 40% to 90% |
| 6 hours at $6.8 \leq pH \leq 7.5$ | >70% | microgranules dissolved relative to the total weight before dissolution.

5. Galenic form according to claim 1 characterized in that the gastroresistant microgranules consist of a neutral granular carrier coated with an active layer consisting of a mixture of 5-nitroimidazole derivative and a binding agent, and of a gastroresistant external layer.

6. Galenic form according to claim 5 characterized in that the gastroresistant external layer comprises excipients ensuring the resistance of the coating to pH values of between 4.5 and 5.5, chosen from poly(meth)acrylic esters, hydroxypropyl methylcellulose and mixtures thereof, and optionally talc and/or one or more plasticizers.

7. Galenic form according to claim 1 characterized in that the prolonged-release microgranules consist of a neutral granular carrier coated with an active layer consisting of a mixture of 5-nitroimidazole derivative and a binding agent, and of a prolonged-release external layer.

8. Galenic form according to claim 7, characterized in that the prolonged-release external layer comprises excipients used for the preparation of prolonged-release microgranules, independent of the pH of the medium in which they act.

9. Galenic form according to claim 8 where the excipients are chosen from the group of poly(meth)acrylic esters, ethyl cellulose and mixtures thereof and optionally talc and or one or more plasticizers and optionally talc and/or one or more plasticizers.

10. Galenic form according to claim 8 characterized in that the gastroresistant external layer comprises at least one excipient which is dependent on the pH of the medium in which the microgranules transit.

11. Galenic form according to claim 10 where the excipient is a pH-dependent poly(meth)acrylic ester.

12. Galenic form according to claim 5 characterized in that the neutral carrier consists of particles of starch or of a mixture of starch and sucrose which have an average diameter of between 400 and 800 microns.

13. Galenic form according to claim 5 where the binding agent is chosen from the group of polyvinylpyrrolidone of various molecular weights, hydroxypropyl methylcellulose of various molecular weights, hydroxypropyl cellulose of various molecular weights, poly(meth)acrylic esters and mixtures thereof.

14. Galenic form according to claim 1 characterized in that the gastroresistant and prolonged-release microgranules have an average diameter of between 0.4 and 1.5 mm.

15. Galenic form according to claim 14 where the average diameter is between 0.8 and 1.1 mm.

16. Galenic form according to claim 1 characterized in that the 5-nitroimidazole derivative is chosen from metronidazole, secnidazole, tinidazole and mixtures thereof.

17. Pharmaceutical composition characterized in that it comprises the galenic form according to claim 1.

18. Pharmaceutical composition according to claim 16 that is in the form of tablets of rapidly-disintegrating tablets or gelatin capsules.

19. Galenic form according to claim 1 wherein the microgranules are gastro-protected microgranules.

20. Galenic form according to claim 1 wherein the microgranules are prolonged-release microgranules.

21. A process of treating infections of the gastrointestinal tract of an animal comprising administering the galenic form of the compound of claim 1 to the animal.

22. The process of claim 21 wherein the infections of the gastrointestinal tract are linked to the presence of Helicobacter pilori.

* * * * *

UNITED STATES PATENT AND TRADEMARK OFFICE
CERTIFICATE OF CORRECTION

PATENT NO. : 5,549,911

DATED : August 27, 1996

INVENTOR(S) : Gérard Leduc and Patrice Debregeas

It is certified that error appears in the above-indentified patent and that said Letters Patent is hereby corrected as shown below:

On cover page, below "Filing Date", insert --Foreign Application Priority Data January 14, 1994 [FR]   France ................94/00394--

Signed and Sealed this

Ninth Day of February, 1999

Attest:

Attesting Officer

*Acting Commissioner of Patents and Trademarks*